(12) United States Patent
Bulent et al.

(10) Patent No.: US 9,555,175 B2
(45) Date of Patent: Jan. 31, 2017

(54) ENDOVASCULAR HEART ASSIST DEVICE

(71) Applicants: Oran Bulent, Konya (TR); Oran Omer Faruk, Konya (TR); Avci Elif Oran, Konya (TR)

(72) Inventors: Oran Bulent, Konya (TR); Oran Omer Faruk, Konya (TR); Avci Elif Oran, Konya (TR)

( * ) Notice: Subject to any disclaimer, the term of this patent is extended or adjusted under 35 U.S.C. 154(b) by 0 days.

(21) Appl. No.: 14/410,110

(22) PCT Filed: Jun. 13, 2013

(86) PCT No.: PCT/TR2013/000181
§ 371 (c)(1),
(2) Date: Dec. 22, 2014

(87) PCT Pub. No.: WO2013/191667
PCT Pub. Date: Dec. 27, 2013

(65) Prior Publication Data
US 2015/0190561 A1 Jul. 9, 2015

(30) Foreign Application Priority Data
Jun. 21, 2012 (TR) .................................. 2012/07222

(51) Int. Cl.
*A61M 1/10* (2006.01)
*A61M 1/12* (2006.01)

(52) U.S. Cl.
CPC ........... *A61M 1/1036* (2014.02); *A61M 1/101* (2013.01); *A61M 1/1005* (2014.02); *A61M 1/1015* (2014.02); *A61M 1/1024* (2014.02); *A61M 1/1086* (2013.01); *A61M 1/122* (2014.02); *A61M 1/125* (2014.02); *A61M 2205/04* (2013.01);
(Continued)

(58) Field of Classification Search
CPC .. A61M 1/1015; A61M 1/1036; A61M 1/122; A61M 1/125
See application file for complete search history.

(56) References Cited

U.S. PATENT DOCUMENTS 5,527,159 A * 6/1996 Bozeman, Jr. .......... A61M 1/10
  415/900
2004/0215050 A1  10/2004 Morello
(Continued)

FOREIGN PATENT DOCUMENTS

EP  2194278 A1  8/2010
WO  WO03/015609 A2  2/2003
(Continued)

*Primary Examiner* — Joseph Dietrich
(74) *Attorney, Agent, or Firm* — Gokalp Bayramoglu

(57) ABSTRACT

The invention is a next generation miniature heart assist device developed in order to maintain the blood circulation in patients with severe heart failure, and is applied endovascularly to the large arteries. This device is technically a kind of synchronous servo electric motor using "direct drive technology". It provides longer battery life and high blood flow. Small volume and very low energy consumption provide a much longer battery life and a high blood flow. As the outer surface of the parts placed into the blood vessel will be completely covered with the endothelial cells and the intima layer of the arteries in time, there will be no foreign surface contacting directly with blood. As a result, no thromboembolic event or any negative effect on the cellular components of blood is expected.

16 Claims, 8 Drawing Sheets

Figure 1:
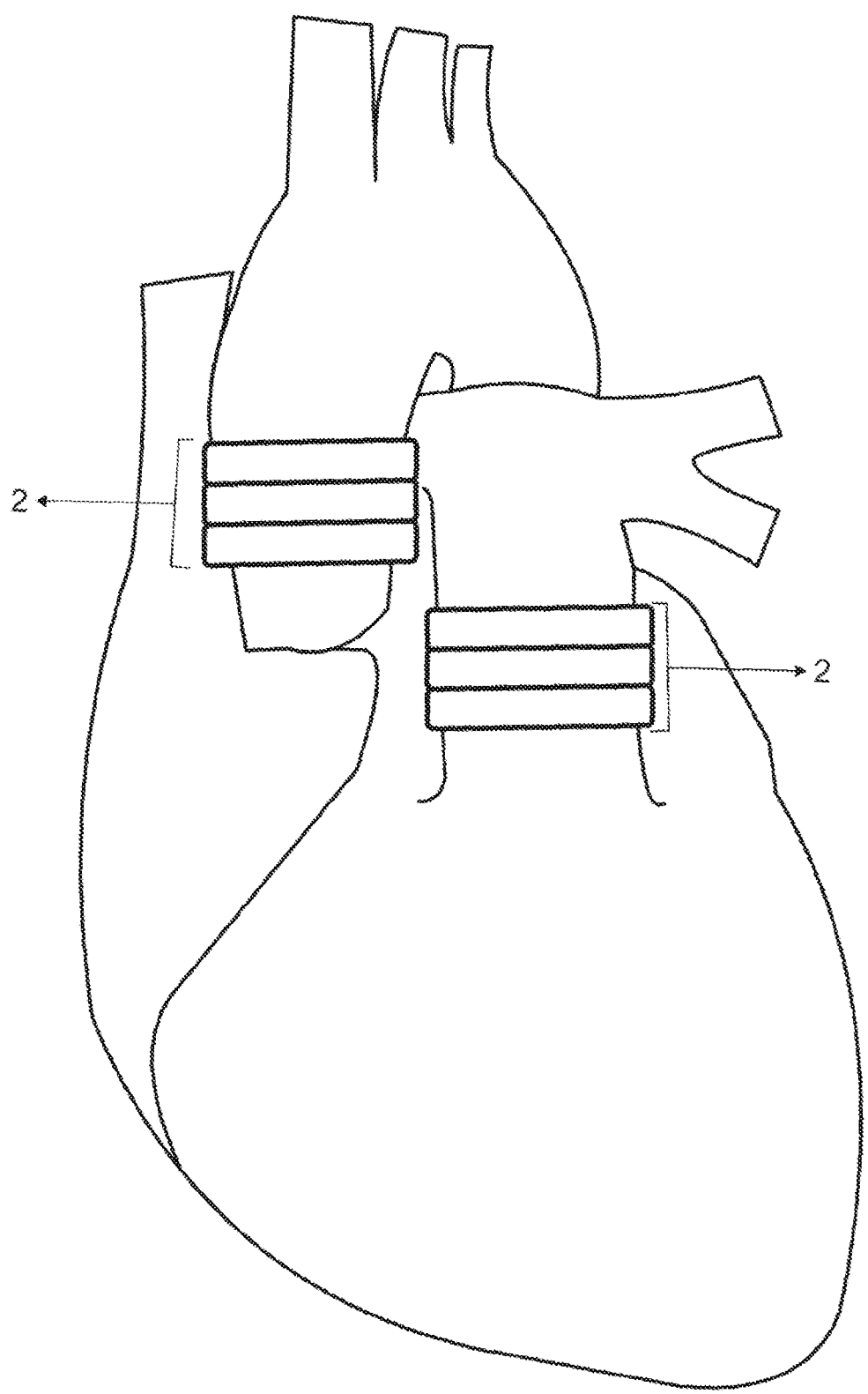

(52) U.S. Cl.
CPC .......... *A61M 2205/3344* (2013.01); *A61M 2205/8212* (2013.01); *A61M 2230/04* (2013.01); *A61M 2230/06* (2013.01); *A61M 2230/30* (2013.01)

(56) References Cited

U.S. PATENT DOCUMENTS

2010/0076247 A1* 3/2010 Zilbershlag .......... A61M 1/101
 600/17
2011/0275884 A1* 11/2011 Scheckel ............. A61M 1/101
 600/16

FOREIGN PATENT DOCUMENTS

WO WO2008/135988 A2 11/2008
WO WO2010/042008 A1 4/2010

* cited by examiner

ENDOVASCULAR HEART ASSIST DEVICE

TECHNICAL FIELD

The invention is a next generation miniature heart assist device which has been developed in order to maintain the blood circulation in patients with severe heart failure, and is applied endovascularly to the large arteries such as the assending aorta and the pulmonary arteries.

BACKGROUND ART

Heart assist devices are vital devices in heart diseases when heart muscle contractions are insufficient, and there is no respond to medications. Nowadays, due to coronary heart diseases and myokardial infarcts (it is the formation of necrosis as a result of blockage of a coronary artery), tens of thousands of people receive the treatment of heart failure. When the drug treatment is insufficient, a heart transplant becomes necessary. Since finding a donor for a heart transplant is not very easy, heart assist devices kept ready for emergency use have become life-saving. In addition, some heart diseases may lead to heart failure even in newborn infants. For this reason, heart assist devices should be produced in all sizes, including pediatric sizes.

In order to ensure a high quality of life for the heart patients waiting for donor's heart, a number of studies to improve heart assist devices have been made and many different products have been presented to the physicians. Jarvik 2000, Lionheart, Coraide, HeartMate II (Thoratec Corp), Berlin heart and HeartSaver are some of these main products. The latest generation device in this area is DeBakey Heart assist device that has been developed with the help of NASA engineers in the United States by Micormed Company representing new generation devices. The fact that they are small in size and suitable for all ages have made these devices the most ideal for today. As it also requires a less invasive surgical procedure, today, it is preferred by cardiac surgeons as for the patients.

Balloon pumps inserted into the aorta were used for this purpose in the past. It was intended that the balloon inflating and deflating synchronously with the heart would provide additional acceleration to the blood flow in the aorta. Later, air-driven systems have been developed. Compressed air is provided from the compressor and air tank moving with the patient. By moving back and forth when the compressed air inflates and deflates, the membrane produces a power propelling the blood. After a while, electric motor systems have been developed, and these systems were first designed with an electric motor and a snail water turbine adapted to it. There are artificial blood vessels (conduits) entering and leaving the system. One end of vessel is placed into the heart and the other end into the aortic artery, and when the engine runs, it takes blood from the heart and pumps out into the aorta.

Compressed air systems were annoying as they run loudly. Because the efficiency of the engine was low and the engine volume was large in electric motor systems, it was a problem to install it into the patients. Moreover, considering them as high-energy-consuming systems, they significantly restricted the ability of the patients to move.

SHORT DESCRIPTION OF THE INVENTION

It is a heart assist device which is installed endovascularly to one of the large arteries such as the aorta (assending aorta) or the pulmonary arteries, and it is helpful to maintain the blood circulation in patients with severe heart failure. The rotor without rotating shaft provides adequate blood flow propelling the blood with its helical propellers.

This is a device with a rotor which rotates with the heart's contraction (systole) and stops or slows simultaneously during, the relaxation (diastole) period, and this is a next generation miniature endovascular heart assist device which contains a sort of synchronous servo electric motor using "direct drive technology". When compared with its counterparts in its field, it is presented as a different concept with new and outstanding features.

As a result of the proliferation of the intima layer of the arteries that is the innermost layer of veins, and covering the endothelial cells coating the inside of vessels, the outer surface of the parts placed into a blood vessel will be completely covered in a few months. Thus, the foreign surface contacting with blood will be only a rotating rotor and its helical propellers. Consequently, there will be no thromboembolic event or any negative effect on the cellular components of blood.

The device, which consumes less energy and provides longer battery life than its counterparts and with its small volume, extraordinary design and endovascular placement, is an endovascular heart assist device that is small enough to be inserted into a large artery.

THE EXPLANATION OF THE FIGURES

Figure 2:
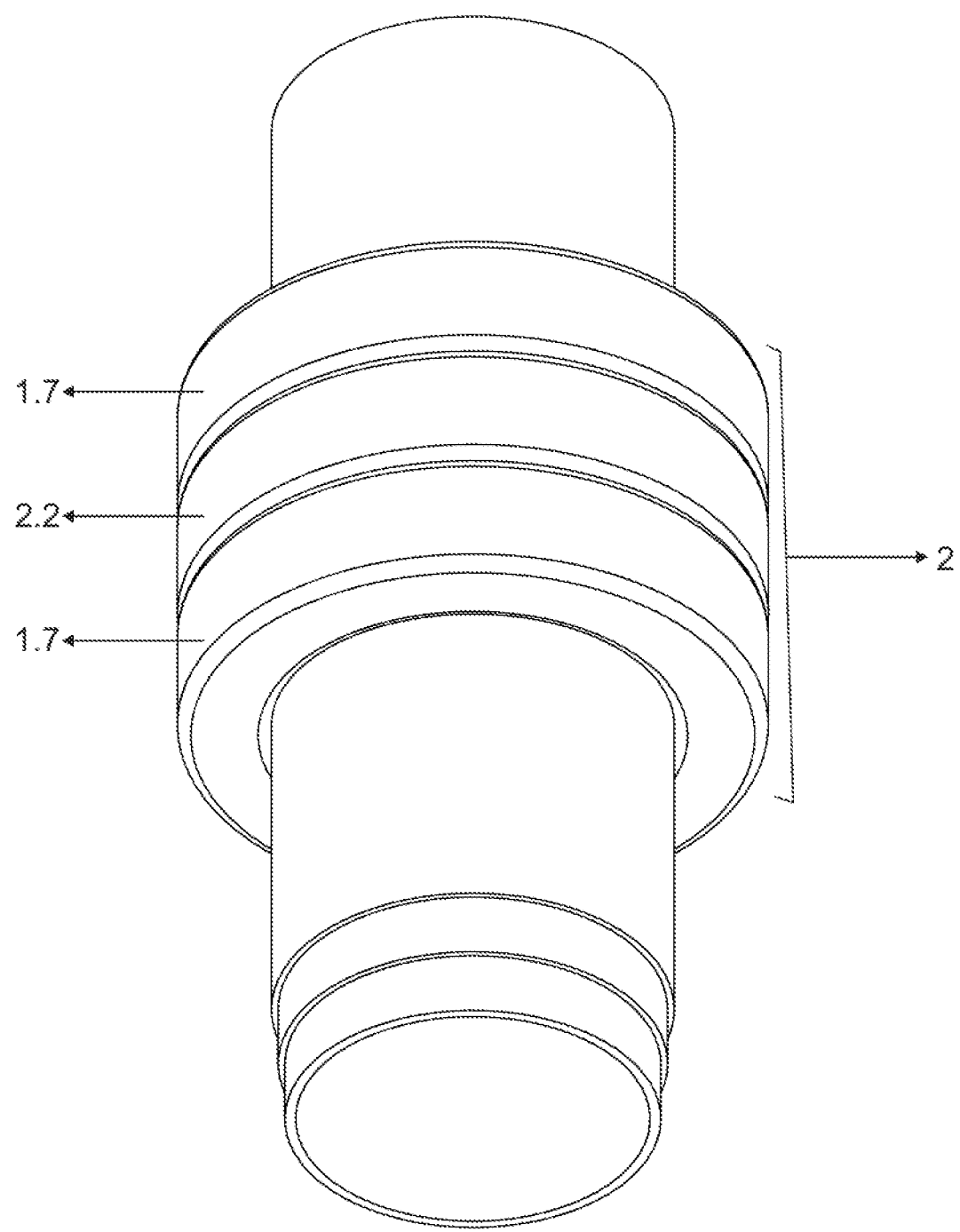
Figure 3:
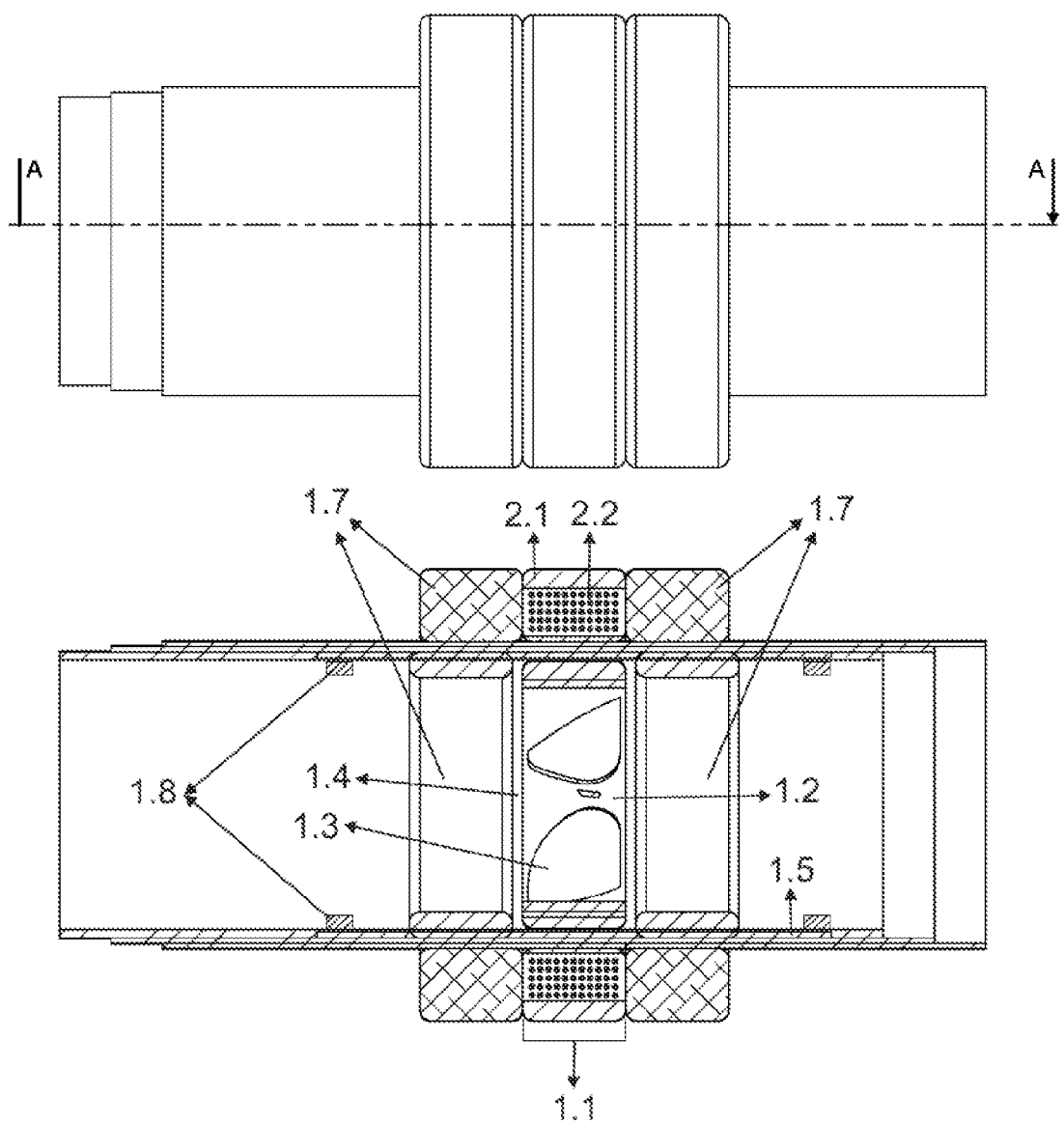
Figure 4:
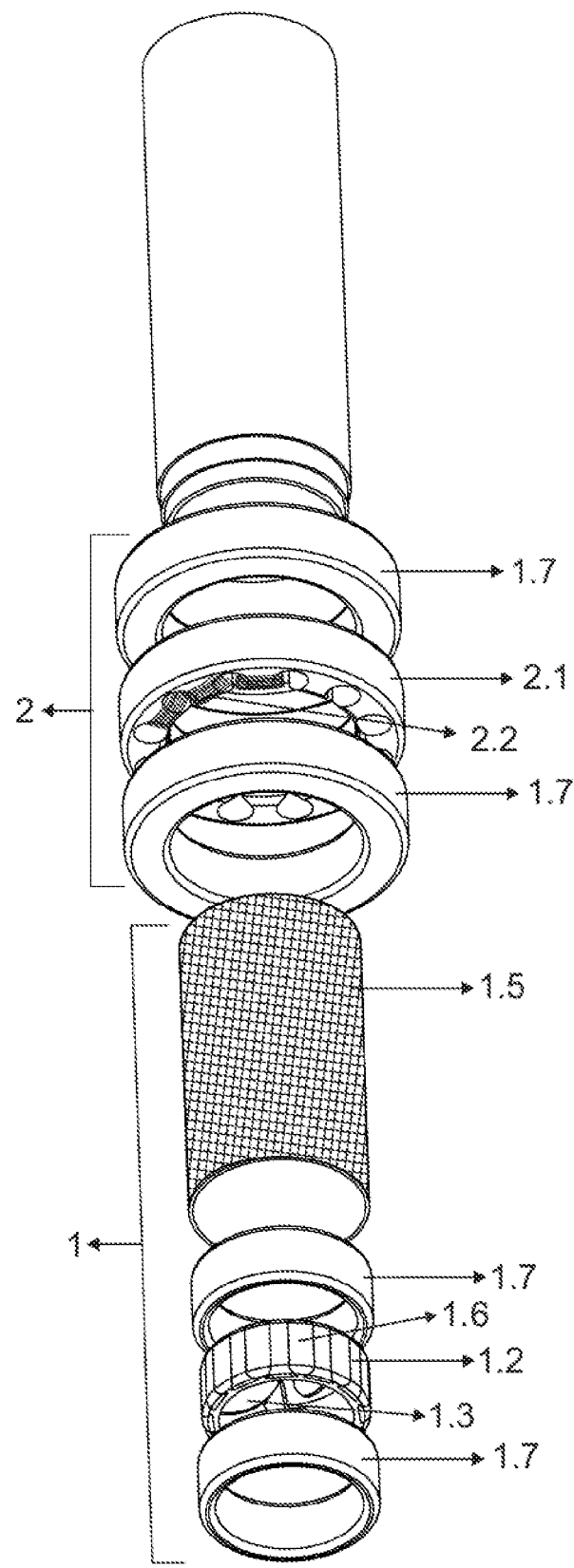
Figure 5:
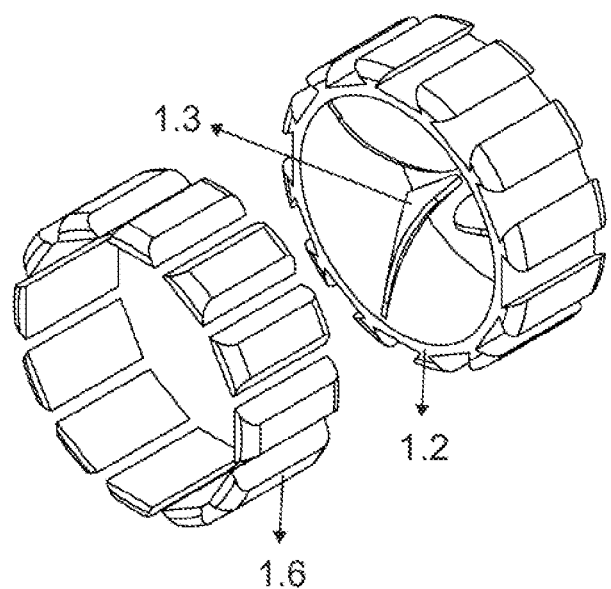
Figure 6:
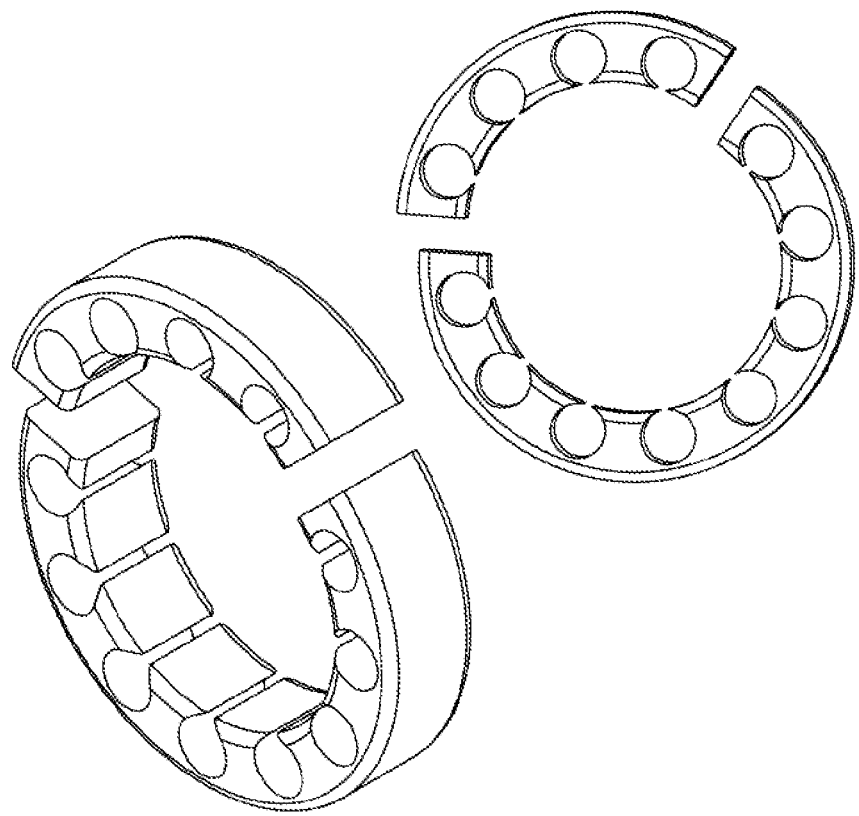
Figure 7:
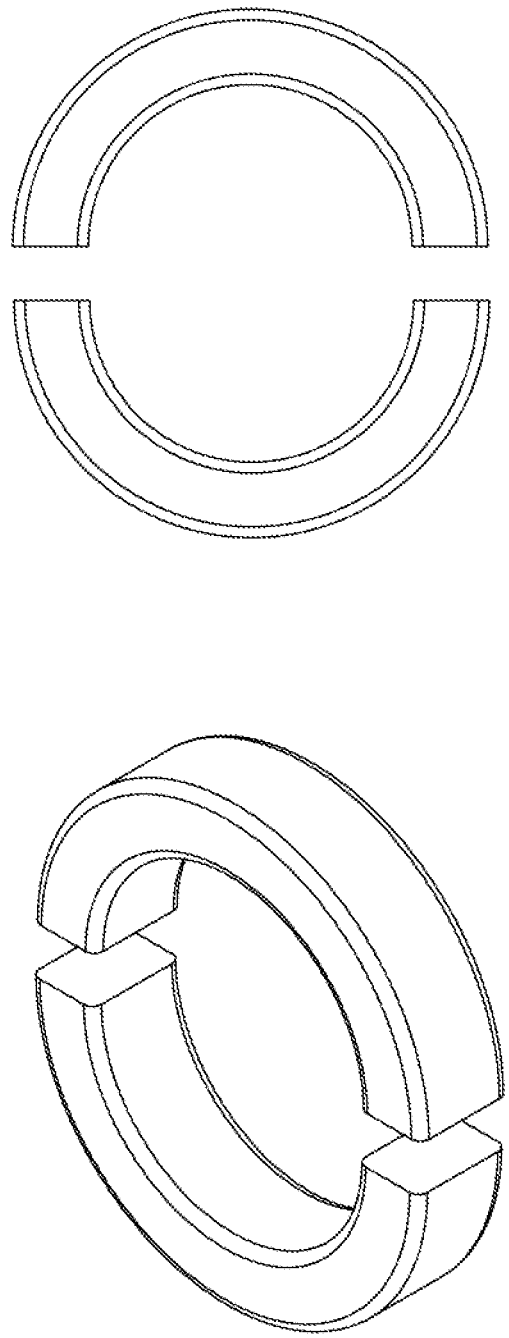
Figure 8:
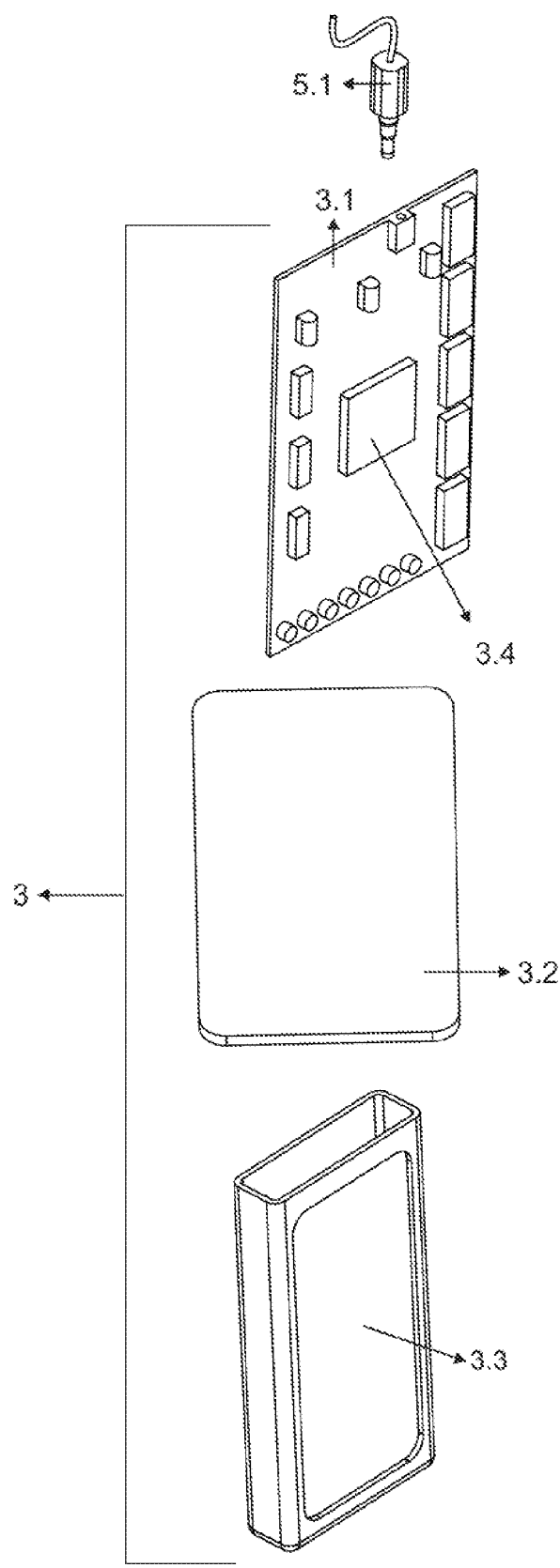
Figure 9:
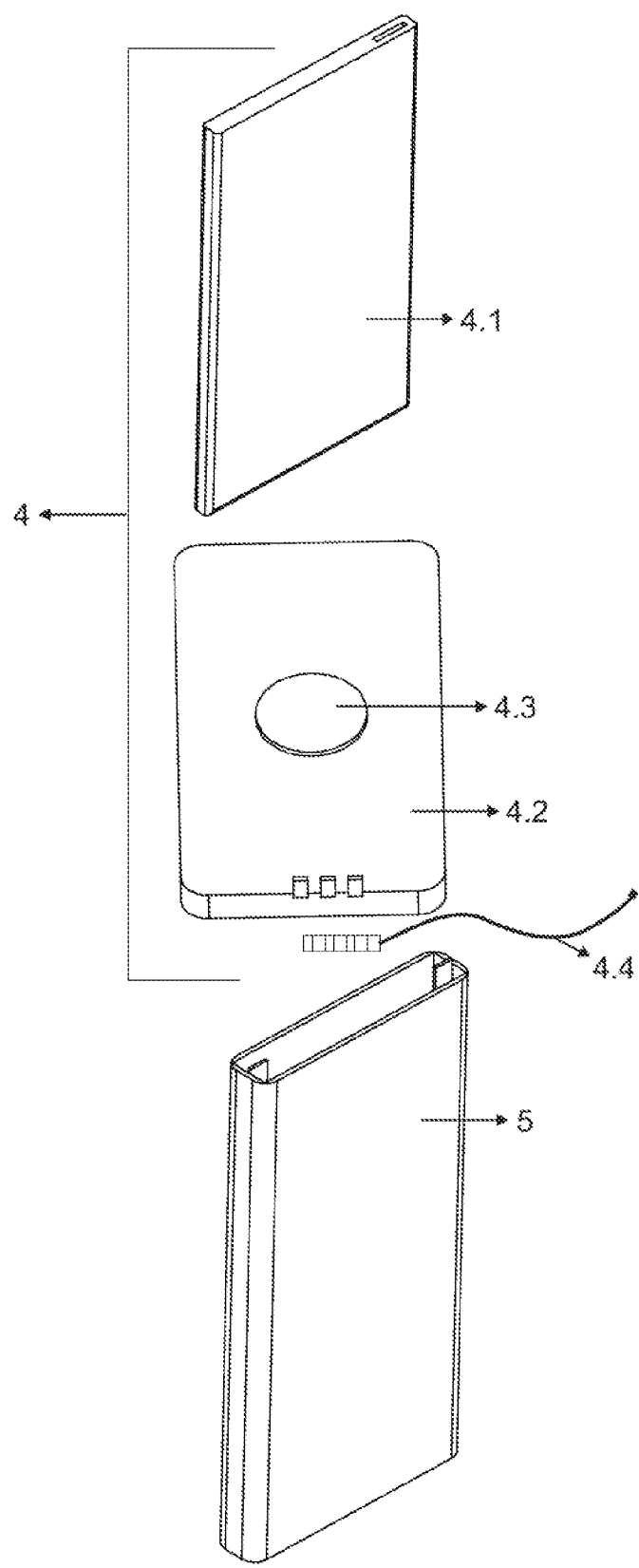

FIG. 1. The View of Endovascular Heart Assist Device Stuck On Pulmonary Artery and Aorta FIG. 2. Overview of Endovascular Heart Assist Device FIG. 3. The View of Exploded Parts of Endovascular Heart Assist Device FIG. 4. The Cross-sectional View of Endovascular Heart Assist Device installed to an artery FIG. 5. Exploded View of Rotor FIG. 6. Exploded View of Stator FIG. 7. Exploded View of Neodymium Permanent Magnet Ring FIG. 8. Control Units FIG. 9. Battery The equivalents of part numerals described in the figures are given below;

1. Endovascular apparatus
 1.1. Motor
 1.2. Rotor
 1.3. Helical Propeller
 1.4. Magnetic bearing
 1.5. Texture cage skeleton
 1.6. Permanent Neodymium Magnet Bar
 1.7. Permanent Neodymium Magnet Ring
 1,8, Pressure Sensors
2. Endovascular Apparatus.
 2.1. Stator
 2.2. Electric coils
3. Control Units
 3.1. Internal Control Unit
 3.2. External Control Unit
 3.3. Touch Screen
 3,4, Microprocessor
4. Batteries
 4.1. Internal Battery
 4.2. External Battery 4.3. Power Transmission Apparatus
4.4. Electrical Power Cable
5. Protective Case
5.1. ECG Connection

DETAILED DESCRIPTION OF THE INVENTION

The invention consists of endovascular apparatus (1), extravascular apparatus (2), control units (3), batteries (4) and protective cover (5) fragments. Endovascular apparatus (1) are composed of an engine (1.1), a rotor (1.2), helical propellers (1.3), a magnetic bearing (1.4), a texture cage skeleton (1.5), permanent neodymium magnet bars (1.6), permanent neodymium magnet rings (1.7) and pressure sensors (1.8). Extravascular apparatus (2) consists of a stator (2.1) and electrical coils (2.2). Control units (3) contain an internal control unit (3.1), an external control unit (3.2), a touch screen (3.3) and microprocessor (3.4) units. The batteries providing the electrical energy requirement of the system (4) includes an internal battery (4.1), an external battery (4.2), power transmission apparatus (4.3) and electric power cables (4.4). The protective cover (5) made of bio-compatible materials that provide protection of apparatus placed into the body, comprises of an ECG connector (5.1) providing data transfer to the internal control unit.

In order to install the heart assist device to the artery as we mentioned about it in the national patent application numbered TR2012/00951 and Patent Cooperation Treaty application numbered PCT/TR2012/00055 we made before, as can be understood from documents, the artery is cut completely from a certain place, and either side of the two cuts is stitched transarterially to the input and output section of the heart assist device. When the documents are examined, it will occur that this device is too large to be placed in the vessel as well as a one-piece integral with the rotor and stator.

However, in the endovascular heart assist device, the subject of this invention, the rotor (1.2) is in the vessel and the stator (2.1) is located outside the vessel, the rotor (1.2) containing helical propellers (1.3) is located in the artery and rotates without contacting the artery on magnetic bearing (1.4). Texture endovascular skeletal cage (1.5) is for supporting rotation field of the rotor. Magnetic bearing (1.4) formed with the help of permanent Neodymium magnet bars (1.0 and permanent neodymium magnet rings (1.7) are fixed onto this texture skeletal cage. The circular power that rotates the rotor in the magnetic field is generated by the current passing through the coils on the stator (2.1) outside the artery. Stators (2.1) are made from overlapped sheets of silicium tin, and there are cavities on it and the coils (2.2) of the electric motor are fixed in the cavities.

The rotor, one of the endovascular apparatus attachment, (1.2) is hollow and includes at least two helical fins on the iron skeleton (1.3). As the points where propellers are attached to the rotor are flexible and foldable, propellers open when the rotor rotates quickly, and provides propulsion and becomes parallel to the inner surface of the rotor when it stops and empties the vessel lumen. Thus, if heart disease heals after a period of time or the rotor stops because of technical reasons, propellers will not constitute an obstacle to the artery blood flow.

If the patient's heart does not heal, then heart assist device will remain connected to the patient's heart until his death and will run and continue to support the heart. The speed of the rotor rotation will be adjusted by the microprocessor (3.4), with the synchronized analysis of the ECG signals in real time, and it will increase or decrease along with them. When the ECG signals are not received, the pre-determined and recorded rotation speed of the engine by the doctor according to the patient's condition will be selected and implemented by the microprocessor (3.4) automatically. When the ECG signals are not technically feasible, there are intense parasites or in case of irregular heart rhythm, (arrhythmia, irregular heartbeat, too fast or too slow heart beats, etc.), the pre-determined and recorded rotation speed of the engine by the doctor according to the patient's condition will be selected and implemented by the microprocessor (3.4) automatically.

Blood pressure will be monitored nonstop with the pressure sensors (1.8) and the data obtained with the artificial intelligence will be processed and optimal rotor speed will be determined with the help of software. There will be settings menu including pre-determined upper and lower limits of rotor speeds.

Pressure sensors (1.8) are also supplied into the artery and blood pressure values will be processed by the artificial intelligence in real-time and then the rotor speed will be increased or decreased by the microprocessor (3.4).

Permanent neodymium magnet rings (1.7) have been placed outside the vessel. Thanks to the magnetic field produced by the permanent neodymium magnet rings (1.7) on either side of both the stator and the rotor, it has been provided to run the rotor and stator safely in their location.

The stator and permanent neodymium rings (1.7) consist of at least two parts. Thus, a heart surgeon can install them as a single piece by wrapping them around the artery like a clamp and assembling them before cutting the pulmonary aorta completely.

In order to facilitate the coverage of endovascular apparatus (1) as a result of intimal proliferation, perforated, durable and bio-compatible wire woven texture cage skeleton (1.5) has been placed into the vein. Other endovascular apparatus (1) are fixed on the texture cage skeleton (1.5).

It is known that the outside of the devices made of nickel-titanium alloy (nitiIon) like a stent and septal occlude is covered by the intima layer and vascular endothelial cells about 6-8 weeks after the placement of the devices. It is estimated that the apparatus (1) of our invention will also be covered naturally with the intima layer and vascular endothelial cells as a result of intimal proliferation. Thus, the contacting surface of blood with foreign material would be limited to only the surface of the spinning rotor, and this would not damage the cellular components of blood.

Apparatus placed into the artery are applied without damaging the patient's heart and vascular physiology. Heart surgeon places the system properly into the artery through a small incision and then the cut is repaired with a proper technique, and the artery remains intact. This heart assist device will provide the patient pulsatile blood flow by running or slowing synchronized with the electrocardiogram (ECG) signals received from the patient. As we know, an individual has a pulsatile blood flow and pulsatile blood flow has many advantages in perfusion the tissues when compared with continuous blood flow.

The invention claimed is:
1. A heart assist device, comprising:
an endovascular apparatus configured to be surgically placed into great arteries; wherein the endovascular apparatus comprises a rotor, which is the rotating part of as motor; wherein the rotor is hollow with at least two helical propellers attached to its inner surface;
a non-vascular apparatus configured to be surgically placed outside the great arteries; and a protective cover configured to provide protection for the endovascular apparatus and the nonvascular apparatus;
wherein the endovascular apparatus further comprises:
a magnetic bearing;
a plurality of pressure sensors; and
a texture cage skeleton;
wherein the magnetic bearing further comprises a plurality of first permanent neodymium magnet rings in front of and behind the rotor and a plurality of permanent neodymium magnet bars; wherein the permanent neodymium magnet bars are located on the outer surface of the rotor;
the endovascular apparatus is assembled;
the texture cage skeleton is made of texture, braided, resistant and bio-compatible material that enhances covering of intimal proliferation.

2. A heart assist device, comprising:
an endovascular apparatus configured to be surgically placed into great arteries; wherein the endovascular apparatus comprises a rotor, which is the rotating part of a motor; wherein the rotor is hollow with at least two helical propellers attached to its inner surface;
a non-vascular apparatus configured to be surgically placed outside the great arteries; and
a protective cover configured to provide protection for the endovascular apparatus and the nonvascular apparatus;
wherein the endovascular apparatus further comprises:
a magnetic bearing;
a plurality of pressure sensors; and
a texture cage skeleton;
wherein the magnetic bearing further comprises a plurality of first permanent neodymium magnet rings in front of and behind the rotor and a plurality of permanent neodymium magnet bars; wherein the permanent neodymium magnet bars are located on the outer surface of the rotor;
the endovascular apparatus is assembled;
the points where the helical propellers are attached to the rotor are flexible and foldable so that the helical propellers are capable of being parallel to the inner surface of the rotor.

3. The heart assist device according to claim 2, wherein the helical propellers open when the rotor rotates quickly, and provides propulsion, and becomes parallel to the inner surface of the rotor when the rotor stops.

4. A heart assist device, comprising:
an endovascular apparatus configured to be surgically placed into great arteries; wherein the endovascular apparatus comprises a rotor, which is the rotating part of a motor; wherein the rotor is hollow with at least two helical propellers attached to its inner surface;
a non-vascular apparatus configured to be surgically placed outside the great arteries; and
a protective cover configured to provide protection for the endovascular apparatus and the nonvascular apparatus;
wherein the endovascular apparatus further comprises:
a magnetic bearing;
a plurality of pressure sensors; and
a texture cage skeleton:
wherein the magnetic bearing further comprises a plurality of first permanent neodymium magnet rings in front of and behind the rotor and a plurality of permanent neodymium magnet bars; wherein the permanent neodymium magnet bars are located on the outer surface of the rotor;
the endovascular apparatus is assembled;
the points where the helical propellers are attached to the rotor are angular to the axis of a vessel in order to provide propulsion in the blood stream while rotating rapidly.

5. The heart assist device according to claim 4, wherein the helical propellers are characterized by the fact that if the rotor stops because of technical reasons, the tips of helical propellers remain parallel to the axis of the vessel so as not to constitute a serious obstacle in front of the hearts left ventricle.

6. The heart assist device according to claim 4, wherein the non-vascular apparatus further comprises a stator, which is a motionless part of the motor; a plurality of electric motor coils; and a plurality of second permanent magnet rings on either sides of the stator, and the stator is made of overlapped sheets of silicium tin.

7. The heart assist device according claim 6, wherein an electric current transferred to the electric motor coils existing in the stator. the permanent neodymium magnet bars on the rotor and the part standing in a space without friction in the magnetic bearing-is created by the second permanent magnet rings located on both sides of the stator and the rotor and operating without friction while rotating.

8. The heart assist device according claim 4, wherein the texture cage skeleton is made of material with magnetic property, wherein the rotor, the helical propellers, and the magnetic bearing are contained within the texture cage skeleton.

9. The heart assist device according to claim 8. wherein the magnetic bearing is characterized by the permanent neodymium magnet ring that causes propulsion by positioning the same poles facing opposite each other, the permanent neodymium magnet bars-located on the rotor.

10. The heart assist device according to claim 4, wherein the motor is characterized by the three-phase, synchronous servo-motor and runs with low-volt alternating current.

11. The heart assist device according to claim 4, wherein the heart assist device further comprises:
a plurality of control units configured to control the heart assist device;
a plurality of batteries configured to supply electrical energy to the heart assist device;
wherein the control unit comprises an internal control unit, an external control unit, a touch screen; wherein the internal control unit further comprises a microprocessor;
wherein the battery comprises an internal, an external battery, a power transmission apparatus, and a plurality of electric power cables;
wherein the protective cover comprises an ECG connector for providing data transfer to the e internal control unit.

12. The heart assist device according to claim 11, wherein the rotational speed of the rotor is adjusted according to synchronous signals received from an ECG link, synchronous signals received from the plurality of pressure sensors and the part controlled by the microprocessor according to the settings determined by physicians.

13. The heart assist device according to claim 12, wherein when the synchronous signals from the pressure sensors to the ECG link are not received or the synchronous signals are not technically feasible or in case of irregular heart rhythm, rotation speed of the rotor is controlled by the microprocessor according to a patient-specific pre-determined adjustment made by the physicians.

14. The heart assist device according to claim 13, wherein the pressure sensors measure the arterial blood pressure in real time.

15. The heart assist device according to claim 6, wherein the stator further comprises a plurality of cavities, and the plurality of electric motor coils are fixed in the cavities.

16. The heart assist device according to claim 4, wherein corners of the endovascular apparatus are radius so that blood clots cannot develop on the surfaces of the corners.

\* \* \* \* \*